US010028803B2

(12) United States Patent
O'Neill et al.

(10) Patent No.: US 10,028,803 B2
(45) Date of Patent: Jul. 24, 2018

(54) TOOL SETTING DEVICE AND METHOD OF TRANSFERRING SCALED SETTING INFORMATION TO A TOOL

(71) Applicant: CUSTOM ORTHOPAEDIC SOLUTIONS, INC., Cleveland, OH (US)

(72) Inventors: Peter O'Neill, Shaker Heights, OH (US); Jake Eva, Cleveland, OH (US); Kyle Walker, Cleveland, OH (US)

(73) Assignee: ARTHREX, INC., Naples, FL (US)

( * ) Notice: Subject to any disclaimer, the term of this patent is extended or adjusted under 35 U.S.C. 154(b) by 118 days.

(21) Appl. No.: 15/267,430

(22) Filed: Sep. 16, 2016

(65) Prior Publication Data

US 2017/0079742 A1     Mar. 23, 2017

Related U.S. Application Data

(60) Provisional application No. 62/219,684, filed on Sep. 17, 2015.

(51) Int. Cl.
| *B23Q 17/22* | (2006.01) |
| *A61B 90/50* | (2016.01) |
| *A61B 90/00* | (2016.01) |
| *A61B 17/17* | (2006.01) |
| *A61B 17/34* | (2006.01) |

(Continued)

(52) U.S. Cl.
CPC .............. *A61B 90/50* (2016.02); *A61B 17/17* (2013.01); *A61B 90/08* (2016.02); *A61B 2017/00725* (2013.01); *A61B 2017/3405* (2013.01); *A61B 2017/3407* (2013.01); *A61B 2034/105* (2016.02); *A61B 2090/0807* (2016.02); *A61B 2090/0811* (2016.02)

(58) Field of Classification Search
CPC ......... A61B 90/50; A61B 90/08; A61B 17/17; B23Q 17/22
USPC ............................................ 33/613, 626, 645
See application file for complete search history.

(56) References Cited

U.S. PATENT DOCUMENTS

| 5,465,492 | A * | 11/1995 | Bond ...................... B25F 5/003 |
| | | | 33/275 R |
| 7,000,331 | B2 * | 2/2006 | Kennedy .................. G01B 3/22 |
| | | | 33/626 |
| 8,672,945 | B2 | 3/2014 | Lavallee et al. |

(Continued)

*Primary Examiner* — G. Bradley Bennett
(74) *Attorney, Agent, or Firm* — Karish & Bjorgum, PC

(57) ABSTRACT

A tool setting device includes a base body having longitudinally opposite base top and bottom surfaces laterally bounded by at least one base side surface. At least one setting aperture extends from the base top surface longitudinally downward at least partially through the base body. An elongate setting support slidably fits into a corresponding setting aperture. The setting support includes indicia and a tool engaging feature. A support holding feature is provided for maintaining a longitudinal position of the setting support with respect to the setting aperture. The tool engaging feature is positioned at a predetermined longitudinal distance above the base top surface. The predetermined longitudinal distance bears a direct relationship to the indicia. The tool engaging feature is maintained at the predetermined longitudinal distance through engagement of the setting support with the support holding feature. A method of transferring numerical setting information to a tool is also provided.

21 Claims, 15 Drawing Sheets

(51) Int. Cl.
*A61B 34/10* (2016.01)
*A61B 17/00* (2006.01)

(56) References Cited

U.S. PATENT DOCUMENTS

| | | | |
|---|---|---|---|
| 2004/0092932 | A1 | 5/2004 | Aubin et al. |
| 2009/0270677 | A1* | 10/2009 | Dillon ............... A61B 1/00133 600/106 |
| 2012/0143198 | A1 | 6/2012 | Boyer et al. |
| 2013/0236874 | A1* | 9/2013 | Iannotti ............... B29C 39/02 434/274 |
| 2013/0307529 | A1* | 11/2013 | Baumgartner ......... G01D 5/145 324/207.2 |
| 2014/0018810 | A1* | 1/2014 | Knape ............... A61B 17/1615 606/80 |
| 2017/0071691 | A1* | 3/2017 | Crawford ............... A61B 90/96 |
| 2017/0119406 | A1* | 5/2017 | Triplett ............... A61B 17/16 |
| 2017/0367849 | A1* | 12/2017 | Miller ............... A61B 90/08 |

\* cited by examiner

TOOL SETTING DEVICE AND METHOD OF TRANSFERRING SCALED SETTING INFORMATION TO A TOOL

RELATED APPLICATION

This application claims priority from U.S. Provisional Application No. 62/219,684, filed 17 Sep. 2015, the subject matter of which is incorporated herein by reference in its entirety.

TECHNICAL FIELD

This disclosure relates to an apparatus and method for use of a tool setting device and method and, more particularly, to a method of, and device for, transferring scaled setting information to a tool.

BACKGROUND

In the surgical planning field, presurgical planning is available to assist a surgeon in placing an implant virtually into patient tissue, with the assistance of preoperative imaging and appropriate software. Examples of the provision and use of suitable software are disclosed in U.S. Patent Application Publication No. 2012/0290323, published 15 Nov. 2012 by Wael K. Barsoum et al.; and U.S. Patent Application Publication No. 2012/0141034, published 7 Jun. 2012 by Joseph P. Iannotti et al.; both of which are incorporated by reference herein in their entirety.

Regardless of the software used, presurgical planning can result in a virtual surgical plan that is then optionally embodied in a 3D printed (or other rapid-manufactured) patient-specific physical patient tissue model that allows a user to interact physically with a tangible structure that optionally includes information from a virtual surgical plan. An example of a suitable physical patient tissue model is disclosed in U.S. Patent Application Publication No. 2012 0276509, published 1 Nov. 2012 by Joseph P. Iannotti et al., which is incorporated by reference herein in its entirety.

Optionally, and again regardless of the way in which the patient-specific tissue model is provided, the physical tissue model may be used to physically transfer information from the virtual surgical plan to an adjustable instrument. An example of a suitable transfer of presurgical plan information to an adjustable instrument using a physical tissue model is disclosed in U.S. Pat. No. 9,301,858, issued 5 Apr. 2016 to Wael K. Barsoum et al., which is incorporated by reference herein in its entirety.

As another option, it is possible to transfer numerical settings from presurgical planning software directly to an adjustable surgical instrument without the intermediate step of providing a physical patient tissue model. An example of a suitable transfer of presurgical plan information to an adjustable instrument using a setting stand is disclosed in U.S. Pat. No. 8,926,627, issued 6 Jan. 2015 to Joseph P. Iannotti et al., which is incorporated by reference herein in its entirety.

One type of adjustable/reusable surgical instrument which can be set to correspond with a virtually generated preoperative surgical plan is disclosed in U.S. Pat. No. 9,198,732, issued 1 Dec. 2015 to Joseph P. Iannotti et al. (hereafter referenced as "the '732 patent"), which is incorporated by reference herein in its entirety. The adjustable reusable surgical instrument of the '732 patent will hereafter be referenced as a "tool" or a "surgical tool". In the '732 patent, a landmark guiding structure is provided. At least two locating feet are provided. Each locating foot is laterally spaced from, and indirectly connected to, the landmark guiding structure. A holdaway structure is connected to each locating foot. Each holdaway structure is adjustably connected to the landmark guiding structure to indirectly and adjustably attach the locating foot to the landmark guiding structure in a spaced-apart relationship therewith. A manipulation handle is connected to the landmark guiding structure. The landmark guiding structure is placed in at least one of a desired location and a desired trajectory with respect to the reference surface. Each locating foot is adjusted relative to the landmark guiding structure, via adjustment of the holdaway structure, into guiding contact with a particular portion of a reference surface. Each locating foot is maintained in the guiding contact position, the surgical tool is removed from the reference surface, and the surgical tool is placed with each locating foot in guiding contact with a particular portion of the patient tissue surface corresponding to a particular portion of the reference surface such that at least one of the desired location and desired trajectory of the landmark guiding structure at the reference surface is replicated by the landmark guiding structure at the patient tissue surface.

SUMMARY

In an aspect, a tool setting device is disclosed. A base body has longitudinally opposite base top and bottom surfaces laterally bounded by at least one base side surface. At least one setting aperture extends from the base top surface longitudinally downward at least partially through the base body. An elongate setting support slidably fits into a corresponding setting aperture. The setting support includes indicia and a tool engaging feature. A support holding feature is provided for maintaining a longitudinal position of the setting support with respect to the setting aperture. The tool engaging feature is positioned at a predetermined longitudinal distance above the base top surface. The predetermined longitudinal distance bears a direct relationship to the indicia. The tool engaging feature is maintained at the predetermined longitudinal distance through engagement of the setting support with the support holding feature.

In an aspect, a method of transferring scaled setting information to a tool is disclosed. A tool setting device is provided. A base body has longitudinally opposite base top and bottom surfaces laterally bounded by at least one base side surface. At least one setting aperture extends from the base top surface longitudinally downward at least partially through the base body. An elongate setting support includes indicia and a tool engaging feature. A support holding feature is provided for maintaining a longitudinal position of the at least one setting support with respect to the setting aperture. The setting support is slidably fit into a corresponding setting aperture. A predetermined longitudinal distance bearing a direct relationship to the indicia is obtained. The setting support is slid longitudinally with respect to the base top surface to position the indicia in a relationship with the base top surface reflecting the predetermined longitudinal distance. The tool engaging feature is positioned at the predetermined longitudinal distance above the base top surface through the sliding of the setting support. The setting support engages with the support holding feature to resist longitudinal movement of the setting support with respect to the base top surface. The tool engaging feature is maintained at the predetermined longitudinal distance through engagement of the setting support with the support holding feature. A landmark guiding structure of the tool is placed into a predetermined setting relationship with the tool setting device. A locating foot of the tool is longitudinally adjusted, with respect to the landmark guiding structure, into contact with a corresponding tool engaging feature. The longitudinally adjusted position of the locating foot is maintained with respect to the landmark guiding structure when the tool is removed from the predetermined setting relationship.

In an aspect, a setting stand for transferring numerical setting information to a tool is disclosed. The tool includes an elongate landmark guiding structure having longitudinally spaced proximal and distal guiding ends separated by a guiding shaft and defining a longitudinal axis and at least two locating feet. Each locating foot is laterally spaced from, and indirectly connected to, the landmark guiding structure. The setting stand includes a base body having longitudinally opposite base top and bottom surfaces laterally bounded by at least one base side surface. A plurality of setting apertures are provided. Each setting aperture extends from the base top surface longitudinally downward at least partially through the base body. An orientation feature is spaced apart from each setting aperture. The orientation feature is selectively mated with the landmark guiding structure in a predetermined setting relationship. A plurality of elongate setting supports is provided. Each setting support is slidably fit into a corresponding setting aperture. Each setting support includes indicia and a tool engaging feature. Each setting support selectively contacts a corresponding locating foot when the landmark guiding structure is in the predetermined setting relationship with the setting stand. A plurality of support holding features is provided. Each support holding feature maintains a longitudinal position of a corresponding setting support with respect to the corresponding setting aperture. Each tool engaging feature is positioned at a predetermined longitudinal distance above the base top surface. Each predetermined longitudinal distance bears a direct relationship to the indicia of the corresponding setting support. Each tool engaging feature is maintained at the corresponding predetermined longitudinal distance through engagement of the corresponding setting support with the corresponding support holding feature.

BRIEF DESCRIPTION OF THE DRAWINGS

For a better understanding, reference may be made to the accompanying drawings, in which.

DESCRIPTION OF ASPECTS OF THE DISCLOSURE

Figure 1:
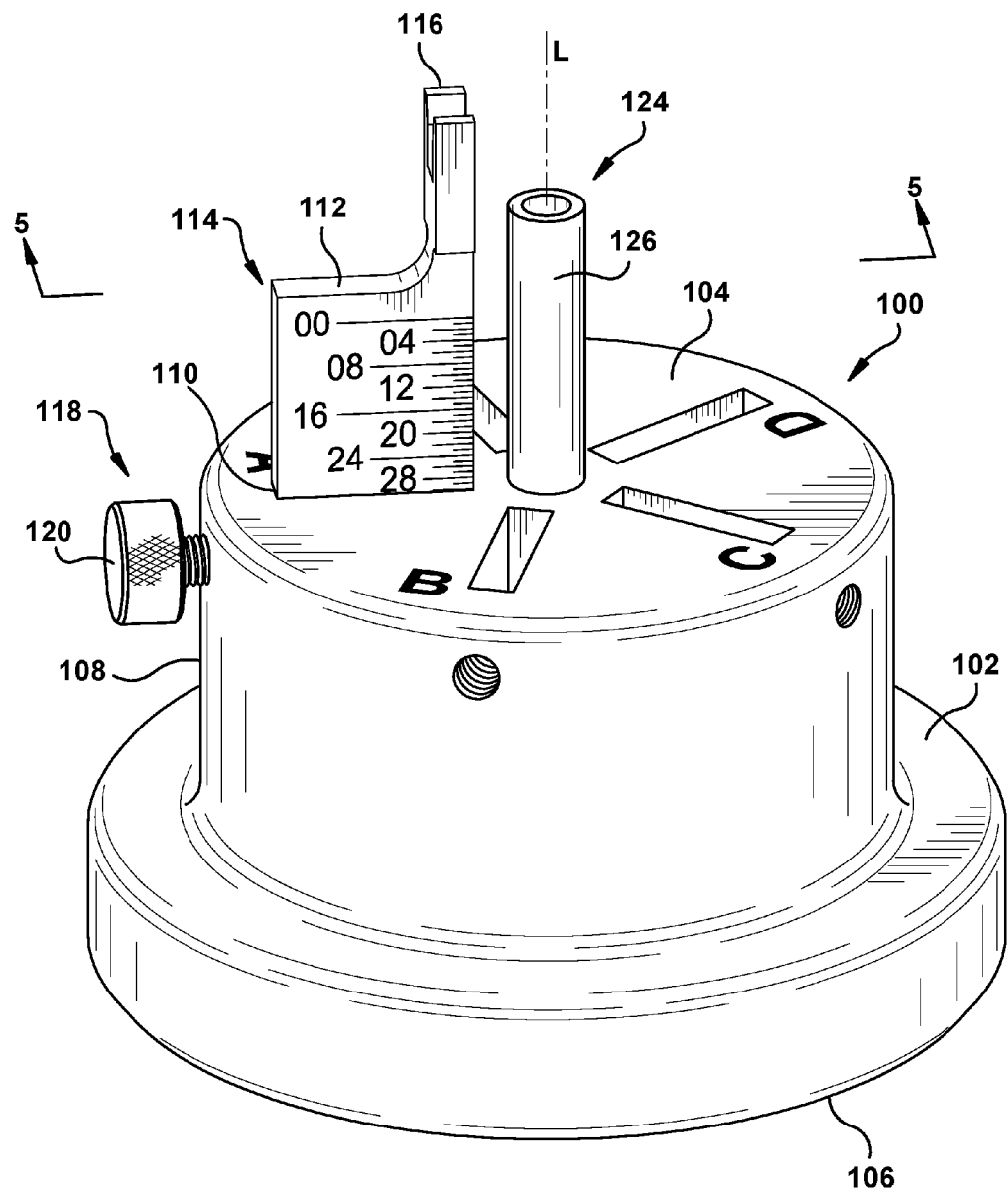
FIG. 1 is a front perspective view of an aspect of present invention in a first configuration.
Figure 2:
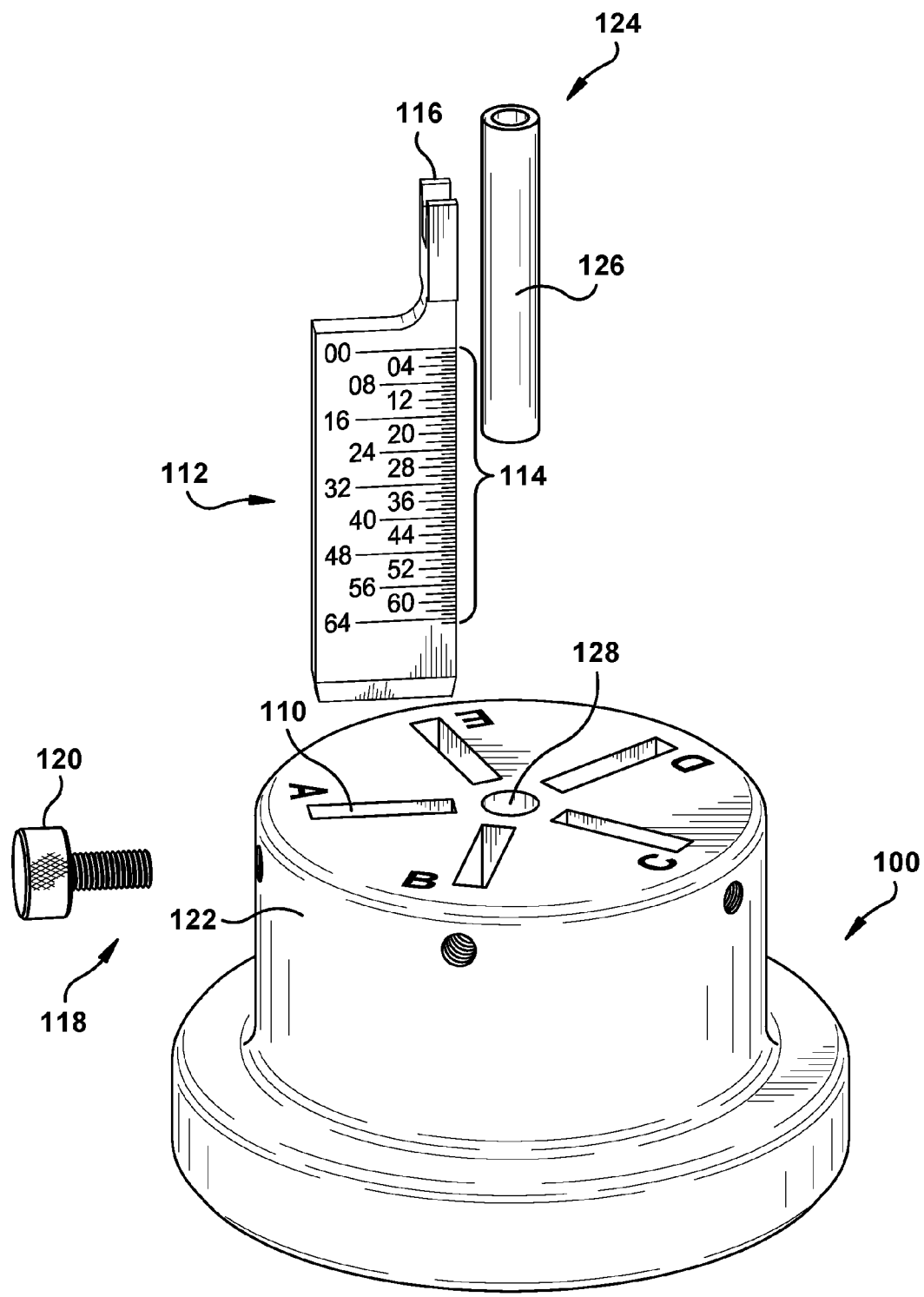
FIG. 2 is an exploded view similar to FIG. 1.

Unless defined otherwise, all technical and scientific terms used herein have the same meaning as is commonly understood by one of skill in the art to which the present disclosure pertains.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper", "left", "right", and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

FIGS. 1-6 depict various views of a first configuration of a tool setting device according to an aspect of the present invention, the tool setting device being referenced below as setting stand 100, for transferring preoperatively planned surgical instrument settings from a software/virtual environment to the surgical tool. The setting stand 100 can function as the previously mentioned "reference surface" for the purpose of assisting with transferring skilled settings information to the tool. A base body 102 has longitudinally opposite base top and bottom surfaces 104 and 106, respectively, laterally bounded by at least one base side surface 108. The base body 102 could be rotationally symmetrical, as shown in the Figures. At least one setting aperture 110 extends from the base top surface 104 longitudinally downward at least partially through the base body 102. The "longitudinal" direction, for this sake of the below description, is substantially parallel to axis "L", or in the top-to-bottom direction, in the orientation of FIGS. 1-2. The "lateral" direction, as used herein, is substantially perpendicular to axis L.

An elongate setting support 112 is slidably fit into a corresponding setting aperture 110. The setting support 112 includes indicia 114 and a tool engaging feature 116. The indicia 114 are shown as a scale with numbers here, but could include letters, symbols, or any other indicator. The indicia 114 could be measurements, or could be relatively arbitrary, as long as the indicia 114 are appropriately coordinated/correlated with the presurgical planning software.

A support holding feature 118 is provided for maintaining a longitudinal position of the setting support with respect to the setting aperture 110. The tool engaging feature 116 is positioned at a predetermined longitudinal distance above the base top surface 104. The predetermined longitudinal distance bears a direct relationship to the indicia 114. For example, the indicia 114 could provide the user with a numerical measurement of the distance of the tool engaging feature 116 above the base top surface 104.

The tool engaging feature 116 is maintained at the predetermined longitudinal distance through engagement of the setting support 112 with the support holding feature 118. The support holding feature 118 could have any suitable configuration. For example, as shown in the Figures, the support holding feature 118 comprises a setting screw 120 extending laterally through the base side surface 108 (e.g., through a screw hole 122 aligned with a chosen setting aperture 110) and into selective compressive engagement with a corresponding setting support 112. As another example, the support holding feature 118 could also or instead comprise a frictional fit between the setting support 112 and a portion of the base body 102 constituting at least one interior wall of a corresponding setting aperture 110, such that a compressive force is exerted upon the setting support 112 by the base body 102 to resist undesired sliding of the support holding feature 118 within the setting aperture 110. One of ordinary skill in the art could readily provide a scheme for maintaining the setting support 112 in a desired longitudinal relationship with the setting aperture 110 for a particular use environment of the setting stand 100.

An orientation feature 124 may be provided to the setting stand 100. When present, the orientation feature 124 may be spaced apart from each setting aperture 110, and may have any desired configuration, to function as will be described below. For example, and as shown in the Figures, the orientation feature 124 may be a shaft 126 extending longitudinally upward from the base top surface 104. As another example, the orientation feature 124 may also or instead include a bore 128 extending longitudinally downward at least partially through the base body 102.

Figure 3:
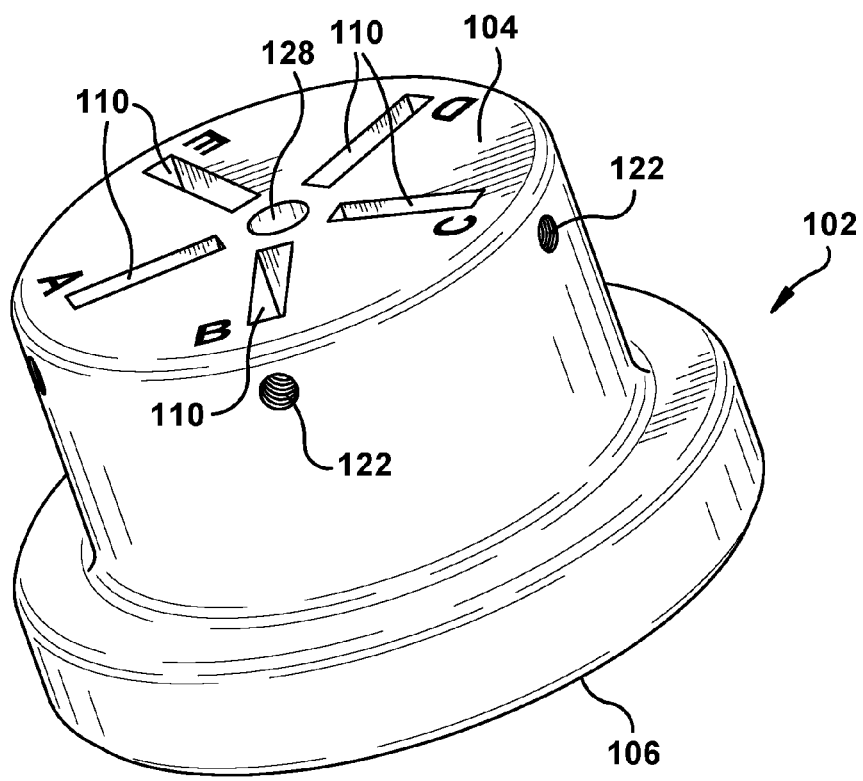
FIG. 3 is a top perspective view of a component of the aspect of FIG. 1.
Figure 4:
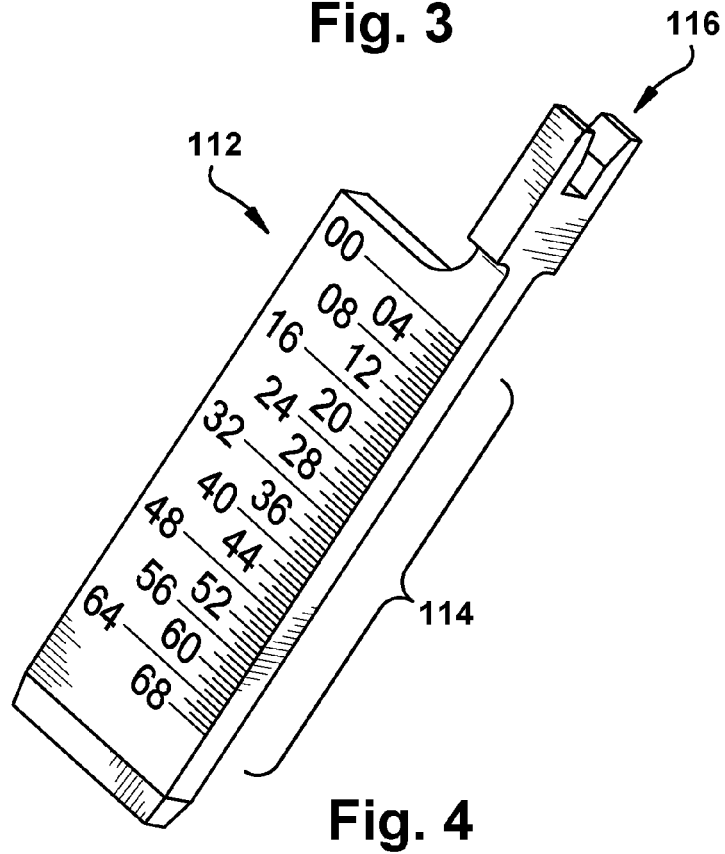
FIG. 4 is a front perspective view of a component of the aspect of FIG. 1
Figure 5:
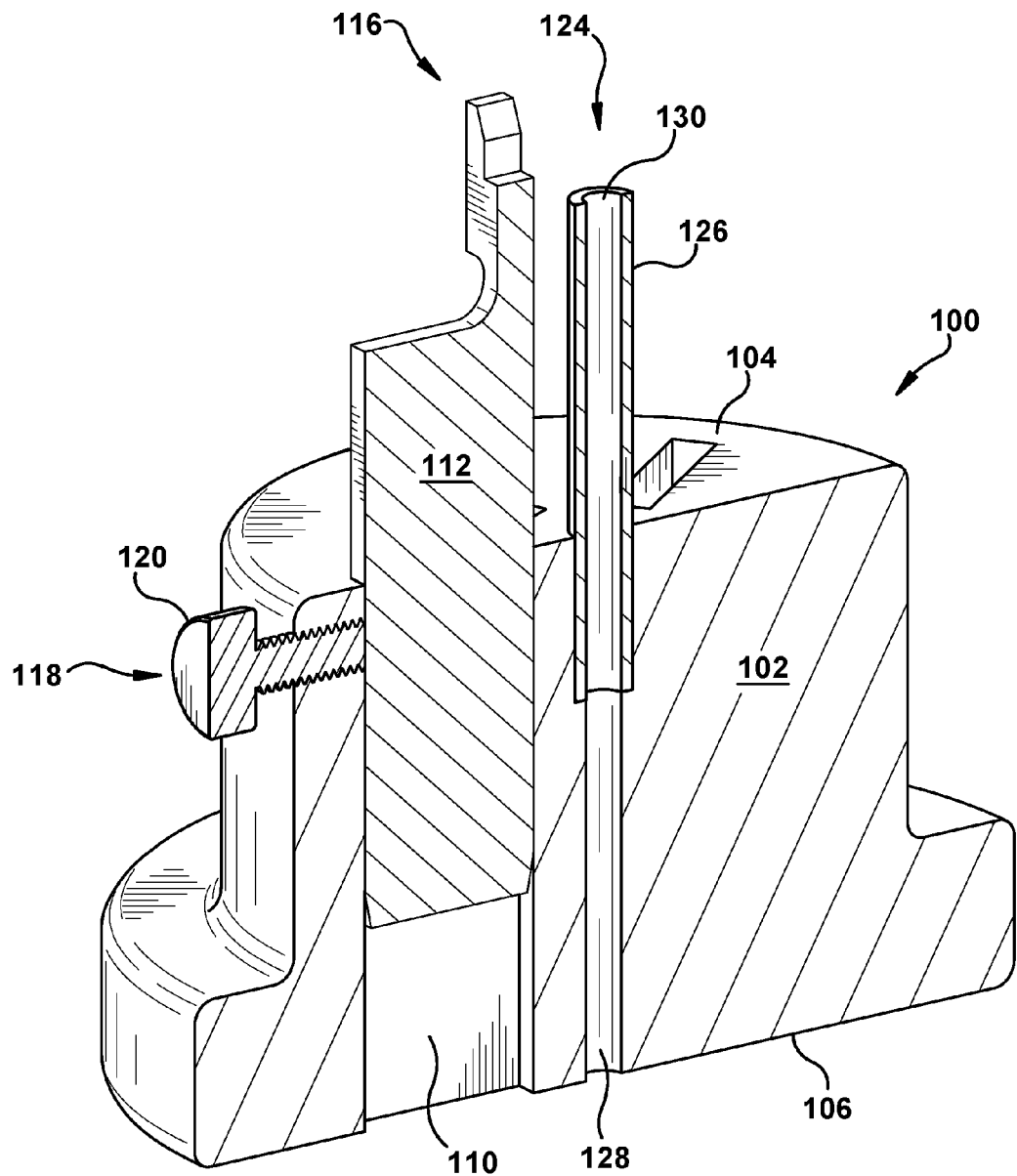
FIG. 5 is a cross-sectional view taken along line 5-5 of FIG. 1.

FIGS. 3-4 depict the base body 102 and setting support 112, respectively, separated from other portions of the setting stand 100. FIG. 5 is a cross-sectional view taken along line 5-5 in FIG. 1. In FIG. 5, the manner in which the setting support 112 slides longitudinally with respect to the setting aperture 110 is shown. In addition, the orientation feature 124 is shown in more detail in FIG. 5. More specifically, FIG. 5 depicts the way in which a stepped bore 128 accepts a tubular shaft 126 including a hollow cylindrical inner diameter. The bore 128 and shaft 126 shown in FIG. 5 collectively define a guidewire lumen 130, which will be discussed in more detail below.

The setting stand 100, as shown in the Figures, includes at least one setting support 112 (one shown in FIG. 6), with each setting support 112 including indicia 114. Each setting support 112 can be adjusted based on desired setting support 112 location settings, such as those determined via suitable preoperative planning software. For many use environments of the setting stand 100, each of the settings will reflect a predetermined longitudinal distance bearing a direct relationship to the indicia 114 of a particular setting support 112. The setting stand 100, and components thereof, is manipulated into a configuration which physically represents one or more of the desired setting support 112 location settings, such as by bringing the indicia 114 of a particular setting support 112 into a physical position with respect to the base body 102 corresponding to the desired setting support 112 location setting for that particular setting support 112. A tool 132, such as, but not limited to, that taught by the '732 patent, may then be adjusted, through interaction with the setting stand 100, to embody the settings, as will be discussed in more detail below with respect to the second configuration of the setting stand 100, shown in FIGS. 7-17. It is contemplated that the first configuration of the setting stand 100, shown in FIGS. 1-6, will operate similarly to that of the second configuration to effectively convey the general working of both configurations to one of ordinary skill in the art, so further description of the first configuration of the setting stand 100, shown in FIGS. 1-6, will be foregone here.

Turning, then, to the second configuration of the setting stand 100, as shown in FIGS. 7-17, the components of the setting stand 100 are substantially similar to those shown in FIGS. 1-6. However, as is implicitly present in the first configuration, the second configuration of the setting stand 100 is shown in FIG. 7-17 as explicitly including a plurality of setting supports 112, each of which is in longitudinally slidable engagement with a selected setting aperture 110 of a plurality of setting apertures 110. That is, each setting support 112 is slidably fit into a different corresponding one of the plurality of setting apertures 110. Accordingly, a tool engaging feature 116 corresponding to each setting support 112 is positioned at a predetermined longitudinal distance above the base top surface 104. The predetermined longitudinal distance of each setting support 112 bears a direct relationship to the indicia 114.

Figure 7:
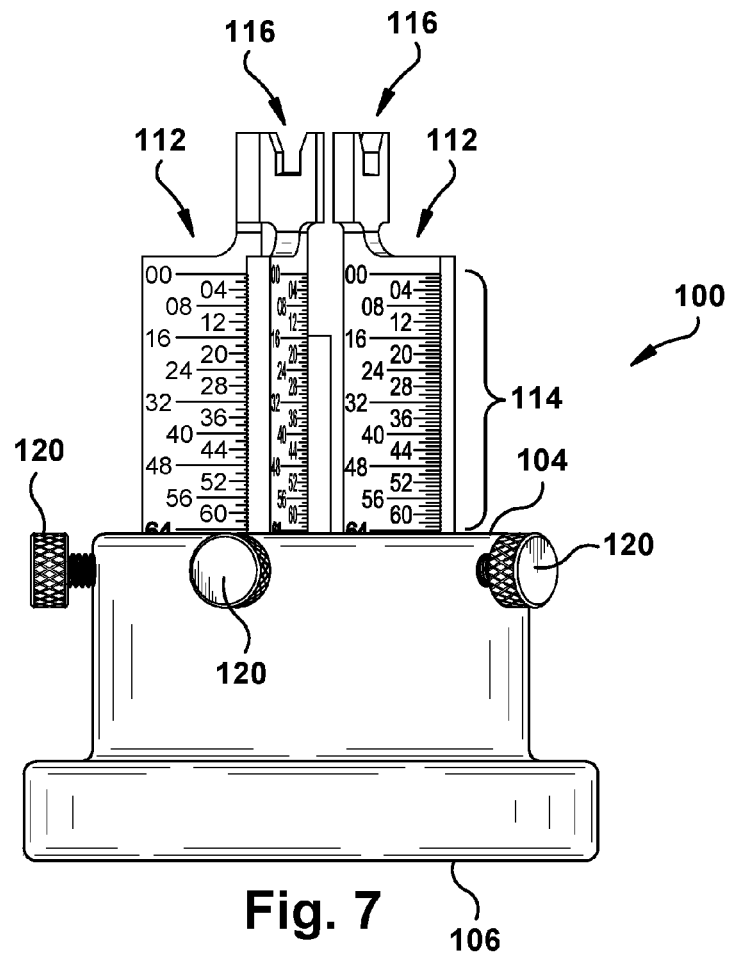
FIG. 7 is a front view of the aspect of FIG. 1 in a second configuration.

For instance, as shown by way of example only in FIG. 7 (which, like all Figures of the present application, is not shown to scale), each setting support 112 is extended forty-four (44) units above a neutral (00) level. The units could be units of measurement, of any desired type, or could be a largely arbitrary scale; the exact nature of the indicia 114 is unimportant, as long as the indicia 114, bear some known relationship to the predetermined longitudinal distance at which the tool engaging feature 116 is to be positioned above the base top surface 104. Each tool engaging feature 116 is maintained at the predetermined longitudinal distance, independently from the longitudinal position of each other tool engaging feature 116 of the plurality of setting supports 112, through engagement of the corresponding setting support 112 with a corresponding support holding feature 118. For example, in the setting stand 100 of the Figures, setting screws 120 are turned within screw holes 122 to come into compressive contact with the setting supports 112 inside the setting apertures 110.

Figure 8:
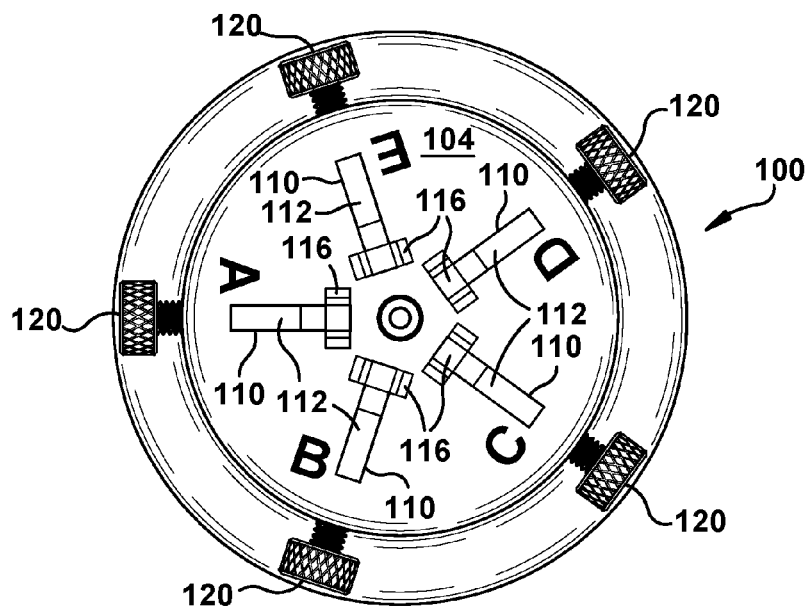
FIG. 8 is a top view of the aspect of FIG. 7.

As shown in FIG. 8, the plurality of setting apertures 110 may be arranged in a circular array upon the base top surface 104. The setting apertures 110 are shown in the Figures as being lettered to assist the user with identifying each individual setting aperture 110 and/or corresponding setting support 112, but other type(s), or no, user-perceptible differentiation between the setting apertures 110 and/or corresponding setting supports 112 may be also or instead provided. It should be noted that, even when a plurality of setting apertures 110, and corresponding setting supports 112, are provided on a particular setting stand 100 one or more of the setting supports 112 could be unused, or even removed from the setting stand 100, depending upon the desired location and number of tool engaging features 116 for a particular use application.

Figure 9:
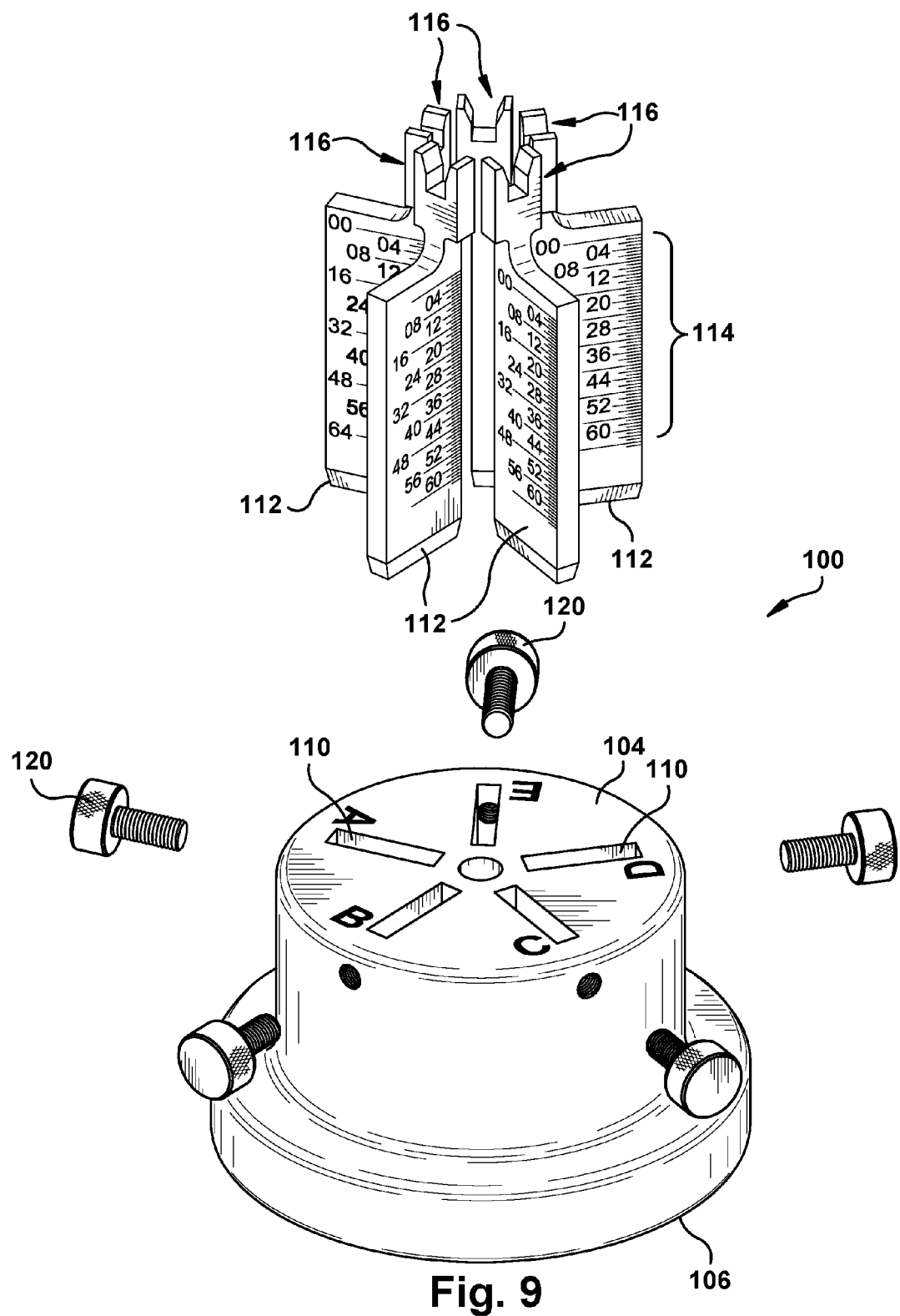
FIG. 9 is an exploded view similar to FIG. 7.
Figure 10:
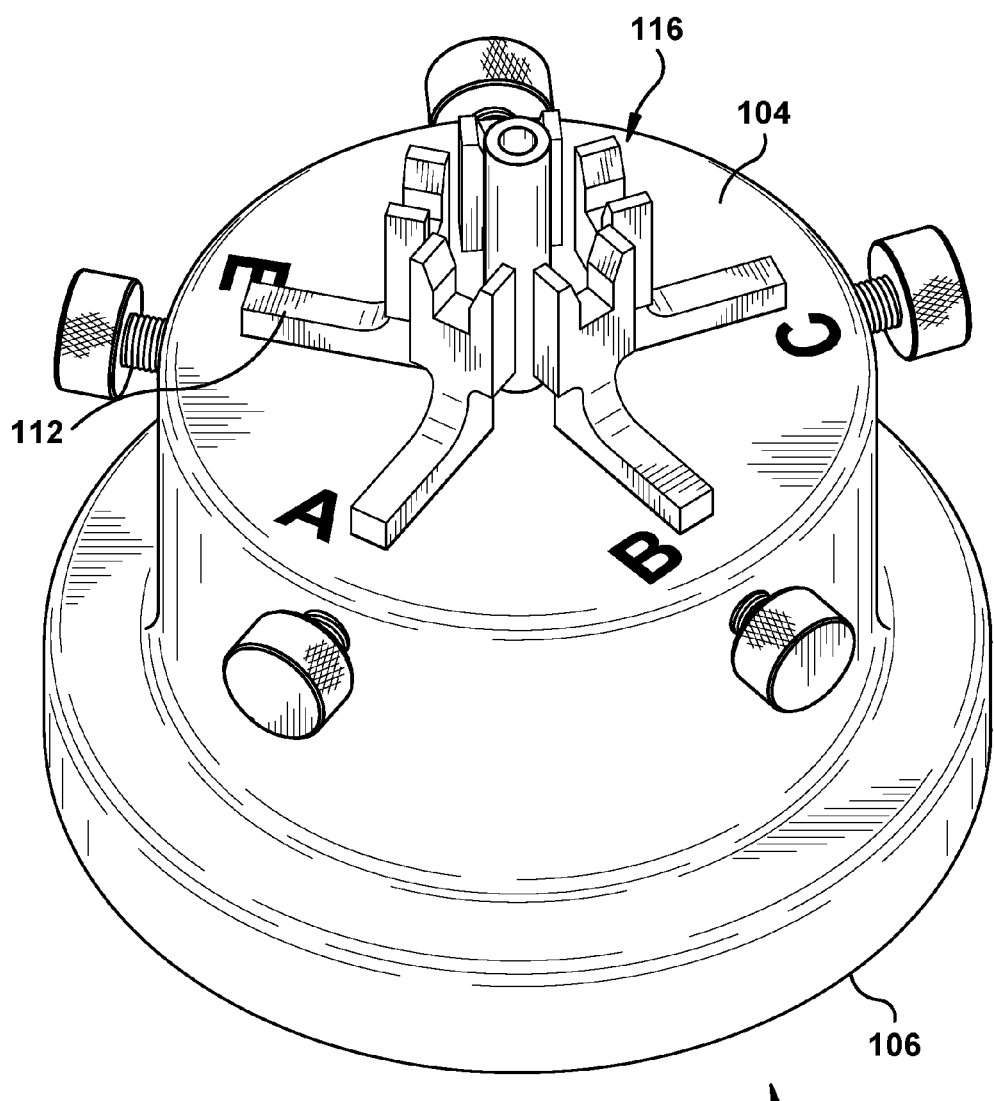
FIG. 10 is a perspective top view of the aspect of FIG. 7.
Figure 11:
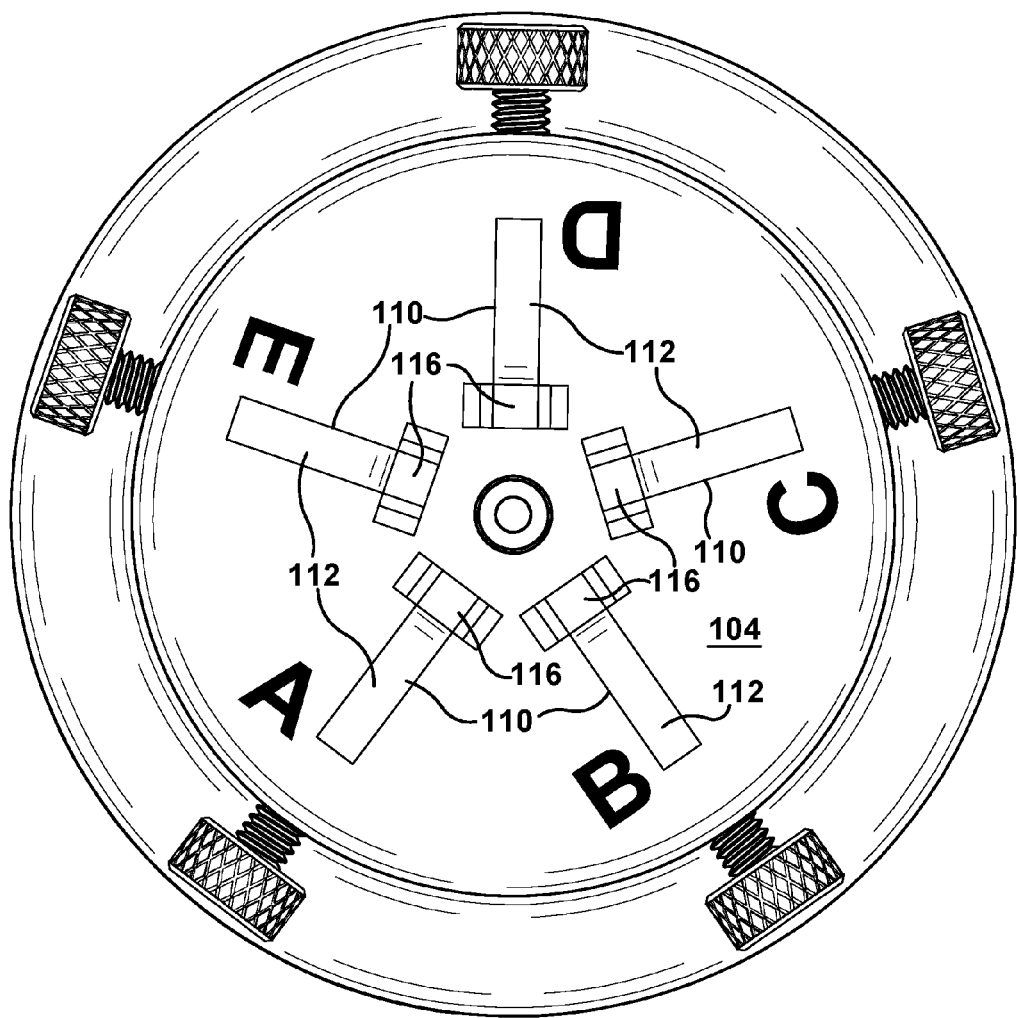
FIG. 11 is a top view of the aspect of FIG. 7.

As can be seen in at least FIGS. 9-11, the base body 102, and thus the corresponding setting supports 112 and setting screws 120, are shown here as being rotationally symmetrical about the shaft 126 and bore 128. However, it is contemplated that one of ordinary skill in the art can provide a setting stand 100, according to the principles of the present invention, having any suitable configuration for transferring skilled setting information to a tool, as will now be discussed with reference to FIGS. 12-17.

As previously noted, it may be desirable to "set" the positions of several components of an adjustable reusable surgical instrument to physically replicate several points corresponding to points on the topography of a particular patient tissue, such as a bone surface into which a landmark (e.g., a guide pin, guidewire, or penetrating tool) is to be placed. During certain types of surgical procedures, it may be desirable to locate a guidewire 134, such as that shown in FIG. 12, at a desired location and trajectory on a native patient tissue, as described in the '732 patent. One way to do so is by passing the guidewire through the bore of a landmark guiding structure which is held at the desired location and trajectory, to impart such to the guidewire 134. However, it may be difficult to reliably place the landmark guiding structure at the desired location and trajectory, given the exigencies of the surgical environment.

Figure 6:
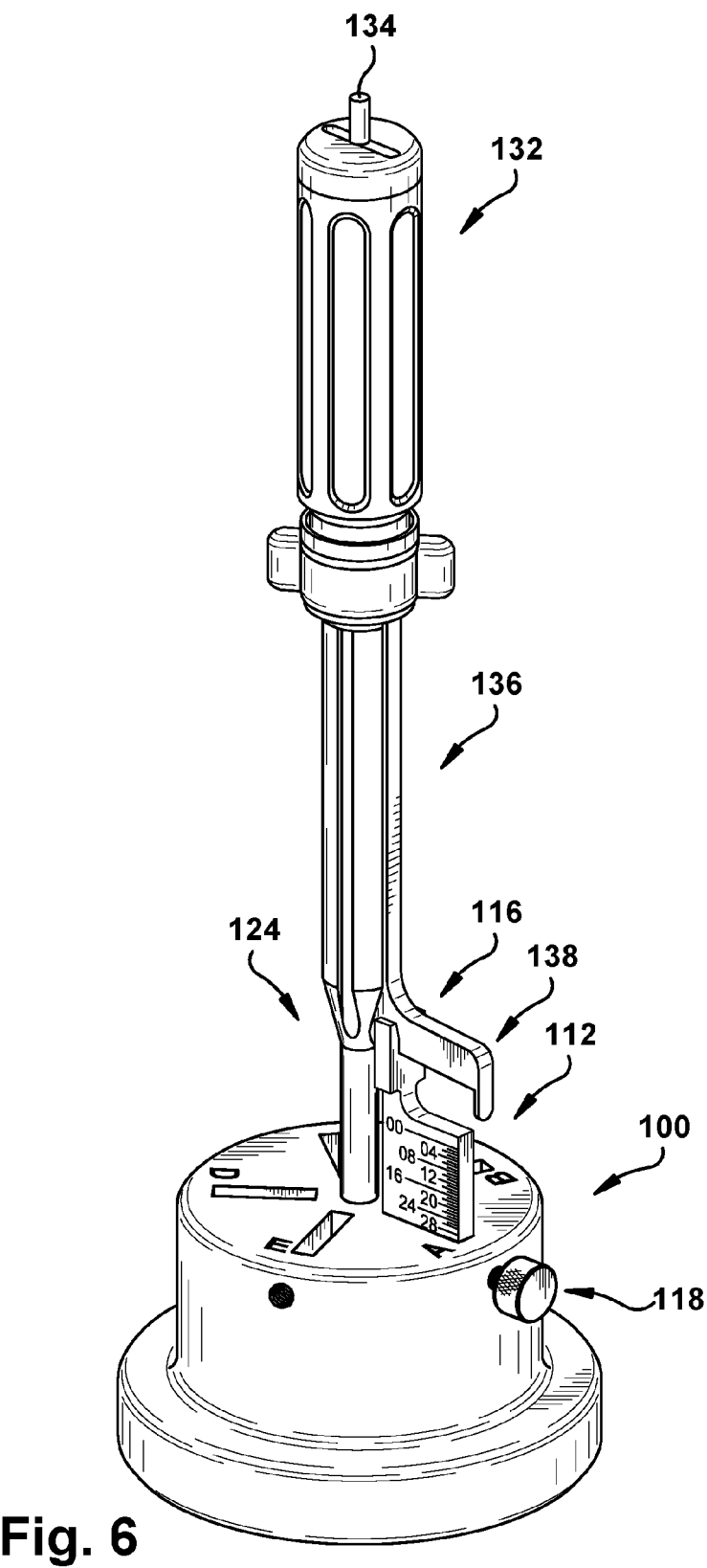
FIG. 6 is a front perspective view of the aspect of FIG. 1 in a first example use arrangement.
Figure 16:
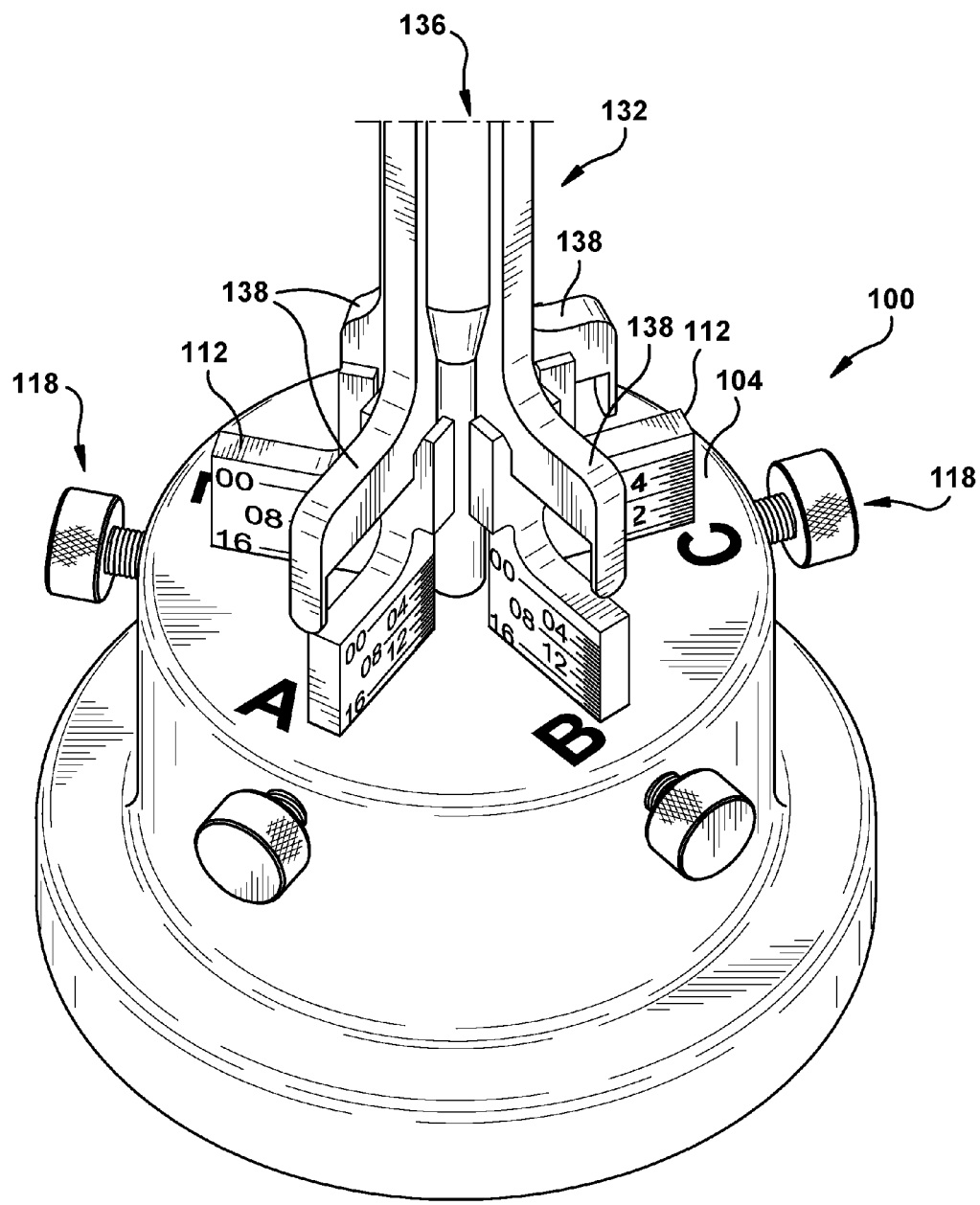
FIG. 16 depicts a first example use configuration of the aspect of FIG. 7.
Figure 17:
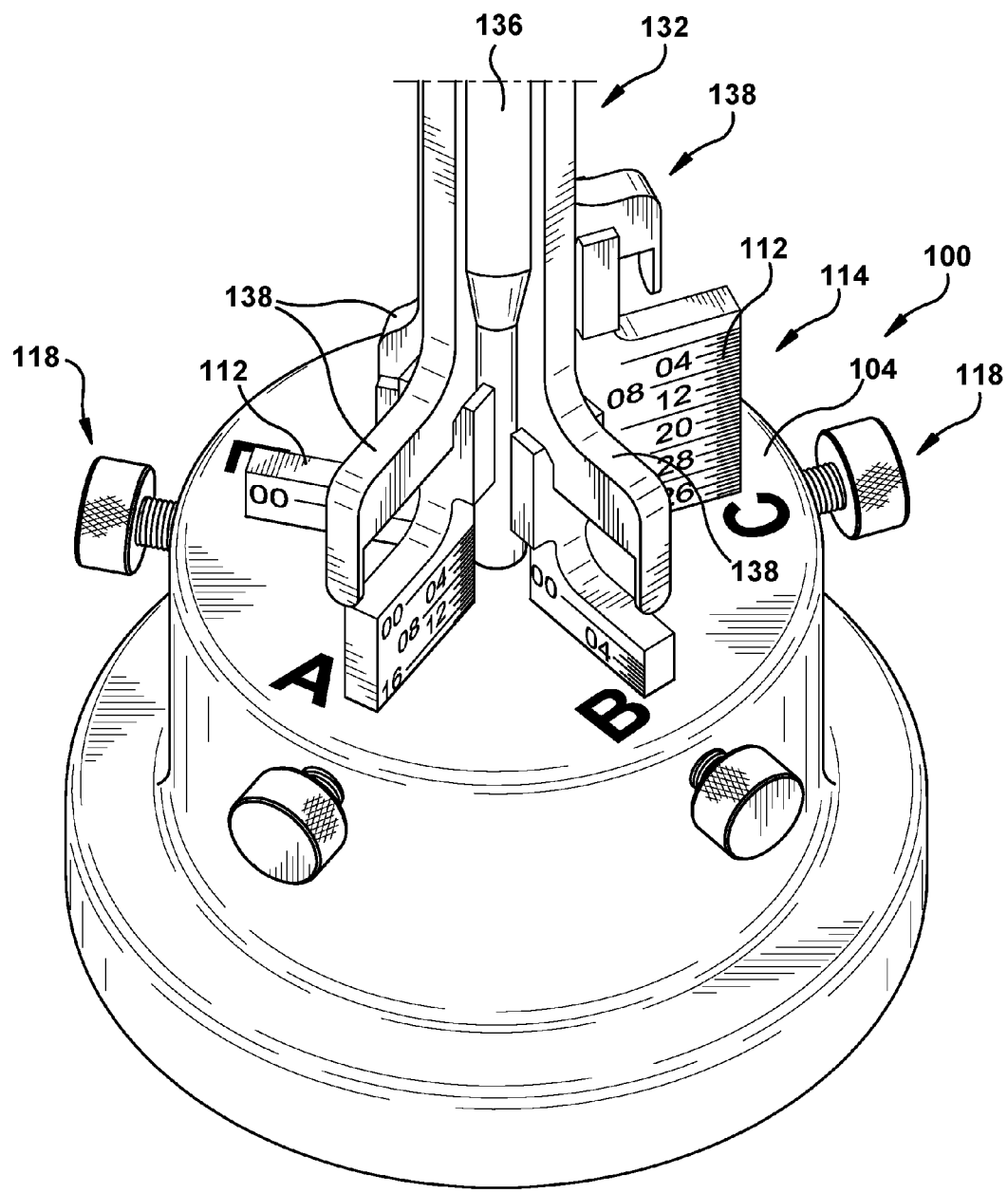
FIG. 17 depicts a second example use configuration of the aspect of FIG. 7.

Therefore, as shown in FIGS. 6 and 16-17, the tool 132 includes landmark guiding structure 136 having at least one locating foot 138 which is laterally spaced from, and longitudinally adjustably connected to, the landmark guiding structure 136. The locating feet 138 of the tool 132 may be adjusted to have a longitudinal relationship to the landmark guiding structure 136 that places the tips of those locating feet 138 at relative positions to create an array of spatially arranged structures bearing a direct relationship corresponding to the local topography of the patient tissue when the landmark guiding structure 136 is at the desired location and trajectory for insertion of the guidewire 134. That is, the locating feet 138 of the tool 132 are adjusted, with the assistance of the setting stand 100, into a physical arrangement such that all of the locating feet 138 are collectively in solid mating contact with the native patient tissue, without the landmark guiding structure 136 rocking or precessing, when the landmark guiding structure 136 is at the desired location and trajectory for insertion of guidewire 134.

If a "properly" set (using the setting stand 100) landmark guiding structure 136 is not nesting firmly and steadily atop the native patient tissue surface, the user will understand that the location and trajectory of the landmark guiding structure 136 with respect to the native patient tissue are incorrect, and some adjustment of the relative positioning of the tool 132 atop the native patient tissue should be performed until the landmark guiding structure 136 is held squarely by the locating feet 138. Through the use of, for example, preoperative imaging and image processing, one of ordinary skill in the art—with knowledge of the desired location and trajectory, the tool 132 structure, and the particulars of the setting stand 100—can provide predetermined longitudinal distances for each of the tool engaging features 116 to hold in relation to the base top surface 104. These predetermined longitudinal distances will assist the locating feet 138 with collectively mimicking, in coarse-grain detail, the local topography of the native patient tissue when the landmark guiding structure 136 is holding the desired location and trajectory for landmark placement.

Figure 12:
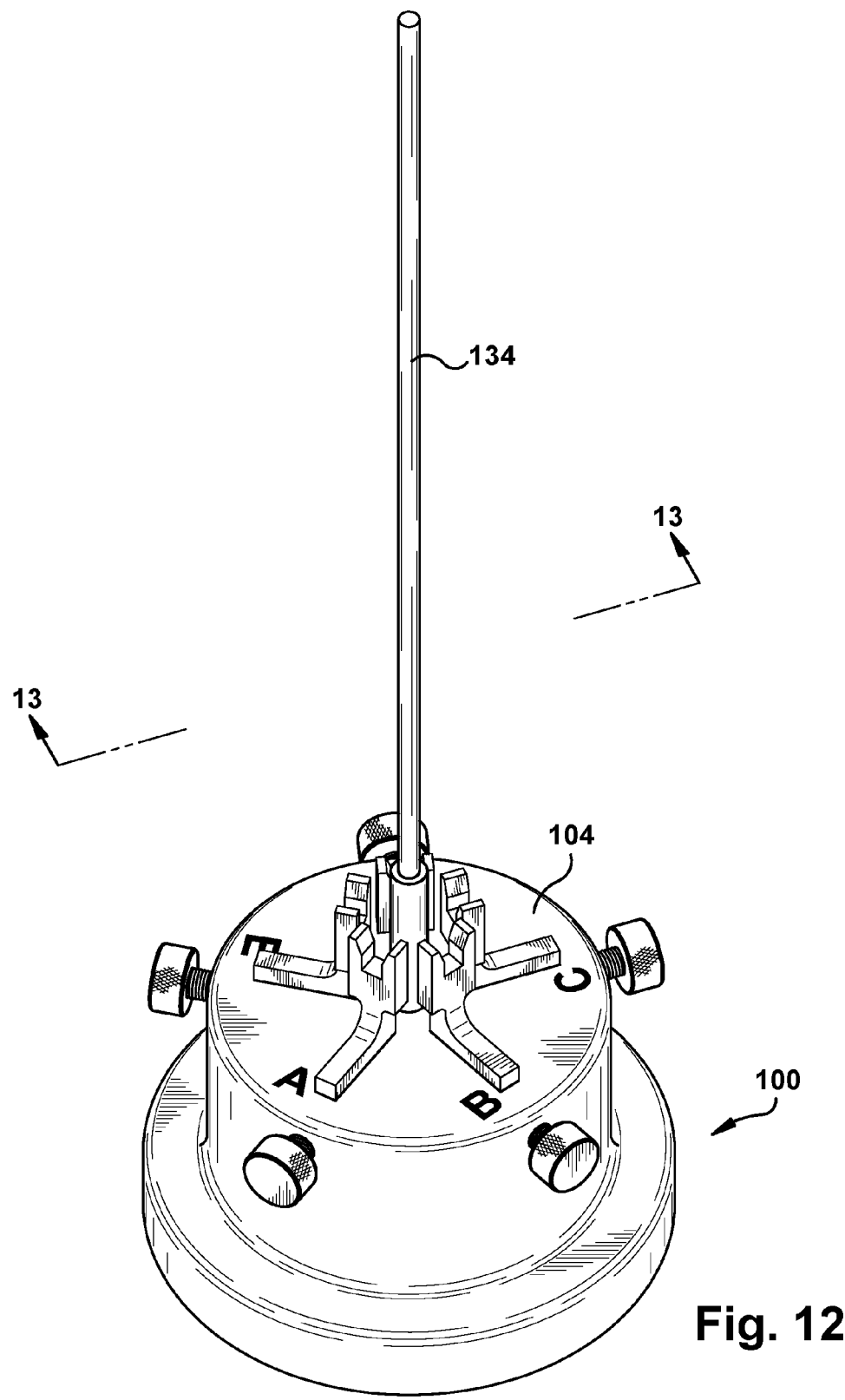
FIG. 12 is a perspective top view of the aspect of FIG. 7.
Figure 13:
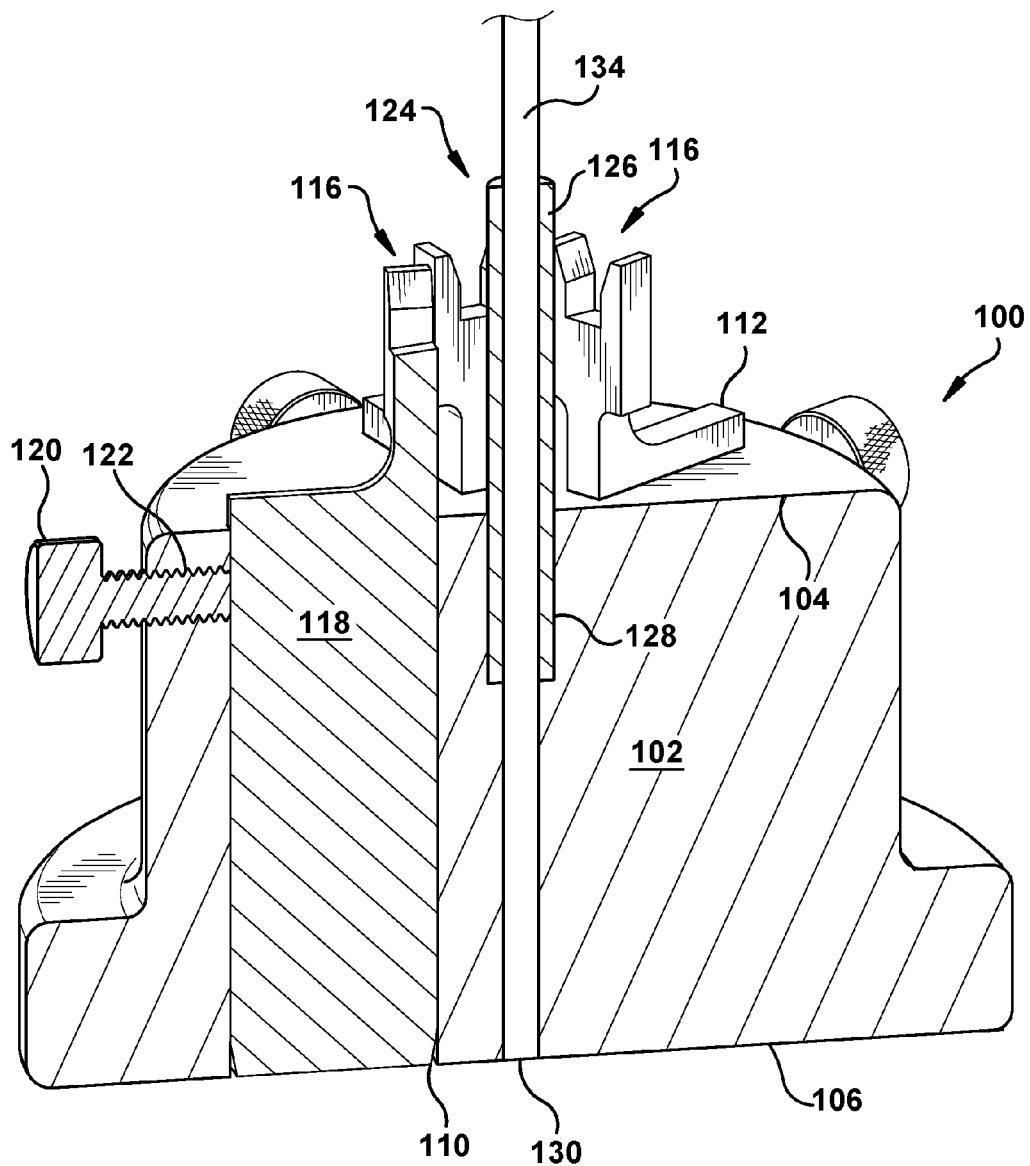
FIG. 13 is a cross-sectional view taken along line 13-13 of FIG. 12.

Regardless of how the predetermined longitudinal distance, bearing a direct relationship to the indicia 114, is obtained, however, the setting stand 100 can be used in a manner similar to that shown in FIGS. 12-17. In FIG. 12, and the cross-sectional view of FIG. 13, the guidewire 134 has been placed into the guidewire lumen 130. As can be seen in these two Figures, the setting supports 112 are each fully retracted into the setting apertures 110 of the setting stand 100. (Using the indicia 114 of the Figures, this corresponds to an initial neutral position of "00", though as can be seen, the tool engaging features 116 are actually located slightly above the base top surface 104 in this example configuration of the setting stand 100. However the slight offset is inconsequential, as long as the predetermined longitudinal distances are adjusted to take the initial positioning into account.)

Figure 14:
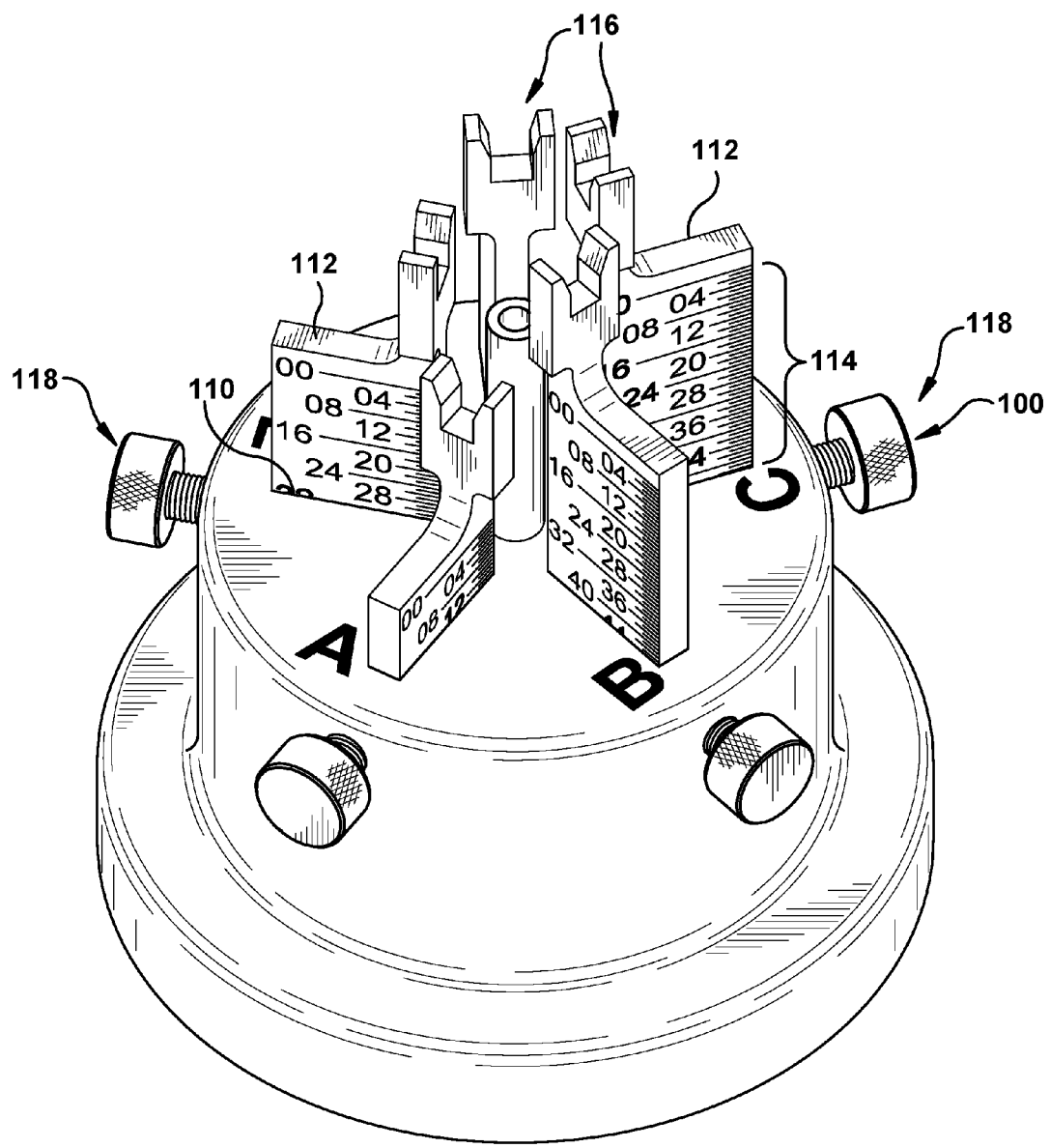
FIG. 14 is a perspective front view of the aspect of FIG. 7.
Figure 15:
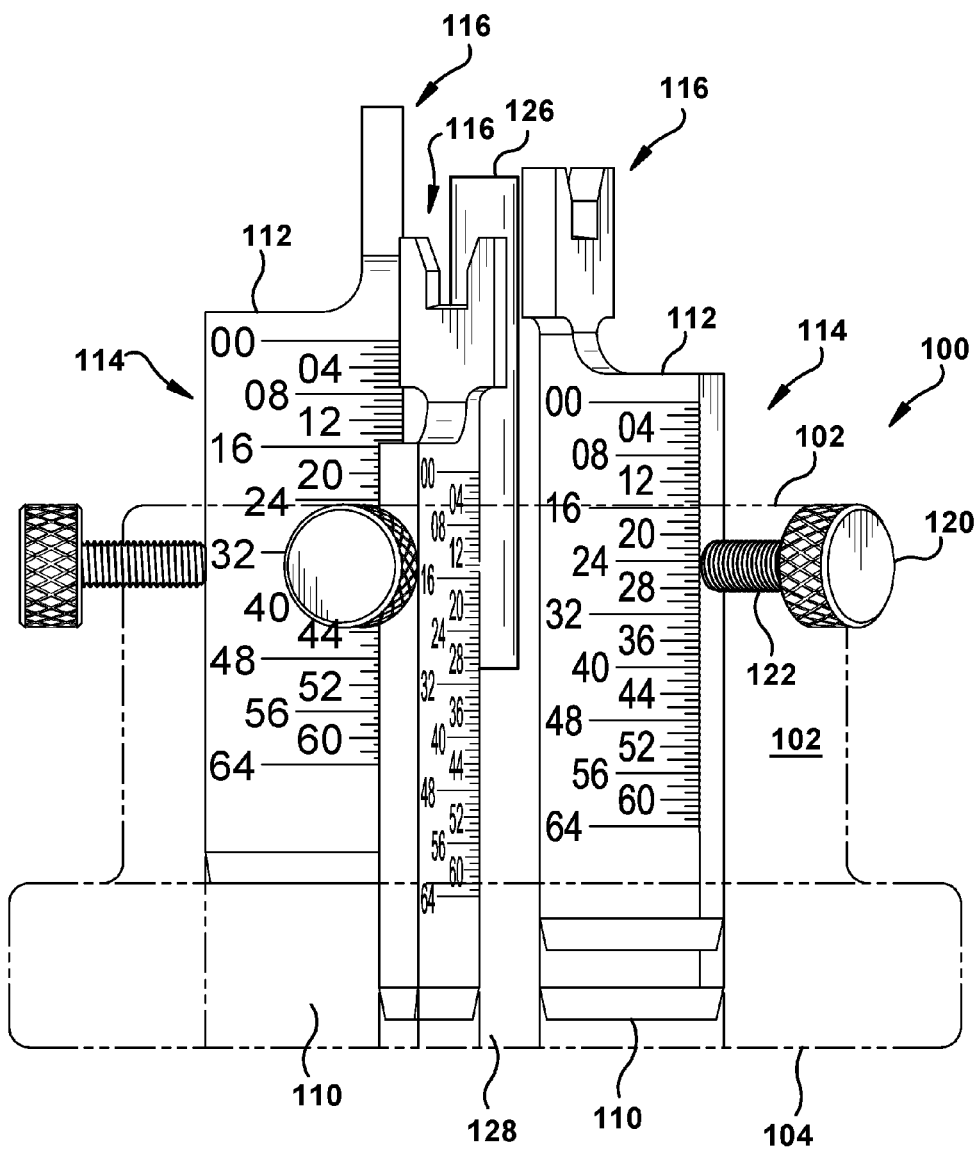
FIG. 15 is a partial front view of the aspect of FIG. 7.

In FIG. 14, each setting support 112 has been slid longitudinally with respect to the base top surface 104 to position the indicia 114 in a relationship with the base top surface 104 reflecting the predetermined longitudinal distance. As can be seen in FIG. 14, each tool engaging feature 116 is raised a slightly different amount than the others above the base top surface 104 (though, again, it is noted that none of the Figures included in this application are shown to scale).

Once the tool engaging features 116 have been positioned at their respective predetermined longitudinal distances above the base top surface 104 through the sliding of the corresponding setting supports 112, each setting support 112 is engaged with the support holding feature 118 to resist longitudinal movement of the setting support 112 with respect to the base top surface 104. Here, that engagement would involve tightening the setting screw 120 in the screw hole 122 and/or a "frictional fit" tight engagement between the setting supports 112 and the setting apertures 110. Regardless of the exact nature of the support holding feature 118, though, each tool engaging feature 116 is maintained at the predetermined longitudinal distance above the base top surface 104 through engagement of the respective setting support 112 with the support holding feature 118.

With reference now to FIGS. 16-17, a landmark guiding structure 136 of the tool 132 may be placed into a predetermined setting relationship with setting stand 100. This placement may involve, for example, providing the setting stand 100 with an orientation feature 124 (such as the provided shaft 126 and/or bore 128) spaced apart from each setting aperture 110. The orientation feature 124 is configured to mate with the landmark guiding structure 136 in one predetermined three-dimensional configuration corresponding to the predetermined setting relationship. For example, as shown in the Figs., the landmark guiding structure 136 can include a central bore which slides over the shaft 126 of the orientation feature 124 (and/or the guidewire 134) in a female-to-male manner. Alternatively, though not shown, the landmark guiding structure 136 could include a protrusion which fits into a bore 128 of an orientation feature 124 in a male-to-female manner. However, no matter the exact nature of the physical structure, the landmark guiding structure 136 of the tool 132 may be brought into mating contact with the orientation feature 124 in order to assist with predictability and reproducibility of precise setting of the tool 132 with the assistance of setting stand 100.

Once the landmark guiding structure 136 is in the desired mating contact with the orientation feature 124 or otherwise placed into a predetermined position with respect to other components of the setting stand 100, a locating foot 138 of the tool 132 can be longitudinally adjusted, with respect to the landmark guiding structure 136, into contact, direct or indirect, with a corresponding tool engaging feature 116 of the setting stand 100. For example, and particularly if the locating feet 138 can be relatively freely slid longitudinally with respect to the landmark guiding structure 136 when unlocked, the locating feet 138 could be allowed to freely slide while the landmark guiding structure 136 is being brought longitudinally downward into engagement with the orientation feature 124. As each locating foot 138 comes into contact with a corresponding tool engaging feature 116, it will "hang up" on a the tool engaging feature 116—that is, the tool engaging feature 116 will inhibit further movement longitudinally downward of that particular locating foot 138 such as by achieving the predetermined setting relationship positioning shown in FIG. 16. Since each tool engaging feature 116 was height-adjusted (for example, according to numerical settings supplied by preoperative setting software) to reflect a particular desired position for locating foot 138, the relative positions of the tool engaging features 116 will directly correspond to a particular height contour profile of a subject patient tissue, for most use environments of the setting stand 100. Therefore, given sufficiently careful choice of the settings of the relative positions of the tool engaging features 116 (achieved with the assistance of the indicia 114), the landmark guiding structure 136, once the tool 132 is in the predetermined setting relationship with the setting stand 100 will then physically embody a desired location and/or trajectory setting for the landmark guiding structure 136, as reflected in the predetermined longitudinal distances above the base top surface 104 of the tool engaging features 116.

The longitudinally adjusted position of each locating foot 138 can then be maintained with respect to the landmark guiding structure 136 when the tool 132 is removed from the predetermined setting relationship. For example, the locating feet 138 can be "locked" in the position shown to "memorialize" the desired trajectory and location setting for physical transfer to the native patient tissue. This locking can happen in any suitable manner, such as those disclosed in the '732 patent.

Once the setting stand 100 and tool 132 have been used with the predetermined longitudinal distances shown in FIG. 16, the setting supports 112 can be readjusted, such as through loosening and then tightening of the support holding features 118, to reflect a different desired location and trajectory setting for the landmark guiding structure 136, such as that shown in FIG. 17. In this manner, a single tool 132 and setting stand 100 can be used for a variety of surgical procedures. It is contemplated that the setting stand 100, and components thereof, could be disposable and/or sterilizable for use in various surgical procedures with a plurality of patients.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A tool setting device, comprising:
   a base body having longitudinally opposite base top and bottom surfaces laterally bounded by at least one base side surface;
   at least one setting aperture extending from the base top surface longitudinally downward at least partially through the base body;
   an elongate setting support, slidably fit into a corresponding setting aperture, the setting support including indicia and a tool engaging feature; and
   a support holding feature for maintaining a longitudinal position of the setting support with respect to the setting aperture;
   wherein the tool engaging feature is positioned at a predetermined longitudinal distance above the base top surface, the predetermined longitudinal distance bearing a direct relationship to the indicia, and the tool engaging feature is maintained at the predetermined longitudinal distance through engagement of the setting support with the support holding feature.

2. The tool setting device of claim 1, wherein the base is rotationally symmetrical.

3. The tool setting device of claim 1, including an orientation feature spaced apart from each setting aperture.

4. The tool setting device of claim 3, wherein the orientation feature is a shaft extending longitudinally upward from the base top surface.

5. The tool setting device of claim 3, wherein the orientation feature is a bore extending longitudinally downward at least partially through the base body.

6. The tool setting device of claim 1, including a plurality of setting supports and wherein the at least one setting aperture is a plurality of setting apertures, each setting support being slidably fit into a different corresponding one of the plurality of setting apertures, and wherein a tool engaging feature corresponding to each setting support is positioned at a predetermined longitudinal distance above the base top surface, the predetermined longitudinal distance bearing a direct relationship to the indicia, and each tool engaging feature is maintained at the predetermined longitudinal distance, independently from the longitudinal position of each other tool engaging feature of the plurality of setting supports, through engagement of the corresponding setting support with a corresponding support holding feature.

7. The tool setting device of claim 6, wherein the plurality of setting apertures is arranged in a circular array upon the base top surface.

8. The tool setting device of claim 1, wherein the support holding feature comprises a frictional fit between the setting support and a portion of the base body constituting at least one interior wall of a corresponding setting aperture.

9. The tool setting device of claim 1, wherein the support holding feature comprises a setting screw extending laterally through the base side surface and into selective compressive engagement with a corresponding setting support.

10. A method of transferring scaled setting information to a tool, comprising:
    providing a tool setting device, including
        a base body having longitudinally opposite base top and bottom surfaces laterally bounded by at least one base side surface,
        at least one setting aperture extending from the base top surface longitudinally downward at least partially through the base body,
        an elongate setting support including indicia and a tool engaging feature, and
        a support holding feature for maintaining a longitudinal position of the at least one setting support with respect to the setting aperture;
    slidably fitting the setting support into a corresponding setting aperture;
    obtaining a predetermined longitudinal distance bearing a direct relationship to the indicia;
    sliding the setting support longitudinally with respect to the base top surface to position the indicia in a relationship with the base top surface reflecting the predetermined longitudinal distance;
    positioning the tool engaging feature at the predetermined longitudinal distance above the base top surface through the sliding of the setting support;
    engaging the setting support with the support holding feature to resist longitudinal movement of the setting support with respect to the base top surface;
    maintaining the tool engaging feature at the predetermined longitudinal distance through engagement of the setting support with the support holding feature;
    placing a landmark guiding structure of the tool into a predetermined setting relationship with the tool setting device;
    longitudinally adjusting a locating foot of the tool, with respect to the landmark guiding structure, into contact with a corresponding tool engaging feature; and
    maintaining the longitudinally adjusted position of the locating foot with respect to the landmark guiding structure when the tool is removed from the predetermined setting relationship.

11. The method of claim 10, wherein placing a landmark guiding structure of the tool into a predetermined setting relationship with the tool setting device includes:
    providing the tool setting device with an orientation feature spaced apart from each setting aperture, the orientation feature being configured to mate with the landmark guiding structure in one predetermined three-dimensional configuration corresponding to the predetermined setting relationship; and
    bringing the landmark guiding structure of the tool into mating contact with the orientation feature.

12. The method of claim 10, wherein providing a tool setting device includes providing a plurality of setting supports, each fitting slidably into a different corresponding one of a plurality of setting apertures; and
    wherein positioning the tool engaging feature at the predetermined longitudinal distance above the base top surface through the sliding of the setting support includes positioning each chosen tool engaging feature of the plurality of setting supports at a corresponding chosen predetermined longitudinal distance above the base top surface through the sliding of the corresponding setting support.

13. The method of claim 12, wherein longitudinally adjusting a locating foot of the tool includes longitudinally adjusting a plurality of locating feet of the tool, each locating foot corresponding to a selected one of the tool engaging features of the setting supports, responsive to a desired trajectory setting for the landmark guiding structure, as reflected in the predetermined longitudinal distances above the base top surface of the tool engaging features.

14. The method of claim 10, wherein maintaining the tool engaging feature at the predetermined longitudinal distance through engagement of the setting support with the support holding feature includes frictionally engaging the setting support with a portion of the base body constituting at least one interior wall of a corresponding setting aperture.

15. The method of claim 10, wherein maintaining the tool engaging feature at the predetermined longitudinal distance through engagement of the setting support with the support holding feature includes rotating a setting screw extending laterally through the base side surface and selective compressive engagement with a corresponding setting support.

16. A setting stand for transferring numerical setting information to a tool including an elongate landmark guiding structure having longitudinally spaced proximal and distal guiding ends separated by a guiding shaft and defining a longitudinal axis and at least two locating feet, each locating foot being laterally spaced from, and indirectly connected to, the landmark guiding structure, the setting stand comprising:
- a base body having longitudinally opposite base top and bottom surfaces laterally bounded by at least one base side surface;
- a plurality of setting apertures, each setting aperture extending from the base top surface longitudinally downward at least partially through the base body;
- an orientation feature spaced apart from each setting aperture, the orientation feature being selectively mated with the landmark guiding structure in a predetermined setting relationship;
- a plurality of elongate setting supports, each setting support being slidably fit into a corresponding setting aperture, each setting support including indicia and a tool engaging feature, each setting support for selectively contacting a corresponding locating foot when the landmark guiding structure is in the predetermined setting relationship with the setting stand; and
- a plurality of support holding features, each support holding feature for maintaining a longitudinal position of a corresponding setting support with respect to the corresponding setting aperture;
wherein each tool engaging feature is positioned at a predetermined longitudinal distance above the base top surface, each predetermined longitudinal distance bearing a direct relationship to the indicia of the corresponding setting support, and each tool engaging feature is maintained at the corresponding predetermined longitudinal distance through engagement of the corresponding setting support with the corresponding support holding feature.

17. The setting stand of claim 16, wherein the base body is rotationally symmetrical, and the plurality of setting supports are arranged in a circular array concentrically around the orientation feature.

18. The setting stand of claim 16, wherein the orientation feature is a shaft extending longitudinally upward from the base top surface for engaging a corresponding bore of the landmark guiding structure.

19. The setting stand of claim 16, wherein the orientation feature is a bore extending longitudinally downward at least partially through the base body for engaging a corresponding shaft of the landmark guiding structure.

20. The setting stand of claim 16, wherein the support holding feature comprises a frictional fit between the setting support and a portion of the base body constituting at least one interior wall of a corresponding setting aperture.

21. The setting stand of claim 16, wherein the support holding feature comprises a setting screw extending laterally through the base side surface and into selective compressive engagement with a corresponding setting support.

* * * * *